(12) United States Patent
Owens et al.

(10) Patent No.: US 7,098,208 B2
(45) Date of Patent: Aug. 29, 2006

(54) INHIBITORS OF AKT ACTIVITY

(75) Inventors: Andrew Pate Owens, Huntingdon (GB); Stanley F. Barnett, North Wales, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/234,784

(22) Filed: Sep. 23, 2005

(65) Prior Publication Data
US 2006/0030564 A1    Feb. 9, 2006

Related U.S. Application Data

(63) Continuation of application No. 10/473,786, filed as application No. PCT/US02/10880 on Apr. 8, 2002, now abandoned.

(60) Provisional application No. 60/282,825, filed on Apr. 10, 2001.

(51) Int. Cl.
*A61K 31/5025*   (2006.01)
*C07D 487/04*   (2006.01)

(52) U.S. Cl. ...................... 514/248; 544/236
(58) Field of Classification Search ............... 544/235; 514/248
See application file for complete search history.

(56) References Cited

U.S. PATENT DOCUMENTS

2004/0106540 A1    6/2004   Barnett et al.

FOREIGN PATENT DOCUMENTS

| WO | WO 98/04559 | 2/1998 |
|---|---|---|
| WO | WO 99/37645 | 7/1999 |
| WO | WO 99/37648 | 7/1999 |
| WO | WO 00/44752 | 8/2000 |
| WO | WO 00/47582 | 8/2000 |
| WO | WO 02/083140 | 10/2002 |
| WO | WO 02/083675 | 10/2002 |

OTHER PUBLICATIONS

McKernan et al., Nature Neuroscience, 3(6):587-592 (2000).
Collins et al., Tetrahedron Letters 41:781-784 (2000).
Nakatani et al., J. Biol. Chem., 274:21528-21532 (1999).
Shiojima and Walsh, Cir. Res., 90:1243-1250 (2002).
Bellacosa et al., Int. J. Cancer, 64:280-285 (1995).
Stambolic et al., Cell, 95:29-39 (1998).
Cheng et al., Proc. Natl. Acad. Sci. U.S.A., 93:3636-3641 (1996).
Cheng et al., Proc. Natl. Acad. Sci. U.S.A., 89:9267-9271 (1992).
Downward, Curr. Opin. Cell Biol., 10:262-267 (1998).
Hanada et al., Biochimica et Biophysica Acta vol. 1697, p. 3-16 (2004).

*Primary Examiner*—Emily Bernhardt
(74) *Attorney, Agent, or Firm*—Matthew A. Leff; Mark R. Daniel

(57) ABSTRACT

The present invention is directed to compounds comprising a triazolo[4,3-b]pyridazine moiety which inhibit the activity of Akt, a serine/threonine protein kinase. The invention is further directed to chemotherapeutic compositions containing the compounds of this invention and methods for treating cancer comprising administration of the compounds of the invention 2 Claims, No Drawings

SEQUENCE LISTING

<160> NUMBER OF SEQ ID NOS: 16

<210> SEQ ID NO 1
<211> LENGTH: 10
<212> TYPE: DNA
<213> ORGANISM: Artificial Sequence
<220> FEATURE:
<223> OTHER INFORMATION: Completely synthetic DNA Sequence

<400> SEQUENCE: 1
ctgcggccgc                                                          10

```
<210> SEQ ID NO 2
<211> LENGTH: 14
<212> TYPE: DNA
<213> ORGANISM: Artificial Sequence
<220> FEATURE:
<223> OTHER INFORMATION: Completely synthetic DNA Sequence

<400> SEQUENCE: 2
gtacgcggcc gcag                                                          14

<210> SEQ ID NO 3
<211> LENGTH: 39
<212> TYPE: DNA
<213> ORGANISM: Artificial Sequence
<220> FEATURE:
<223> OTHER INFORMATION: Completely synthetic DNA Sequence

<400> SEQUENCE: 3
cgcgaattca gatctaccat gagcgacgtg gctattgtg                               39

<210> SEQ ID NO 4
<211> LENGTH: 33
<212> TYPE: DNA
<213> ORGANISM: Artificial Sequence
<220> FEATURE:
<223> OTHER INFORMATION: Completely synthetic DNA Sequence

<400> SEQUENCE: 4
cgctctagag gatcctcagg ccgtgctgct ggc                                     33

<210> SEQ ID NO 5
<211> LENGTH: 24
<212> TYPE: DNA
<213> ORGANISM: Artificial Sequence
<220> FEATURE:
<223> OTHER INFORMATION: Completely synthetic DNA Sequence

<400> SEQUENCE: 5
gtacgatgct gaacgatatc ttcg                                               24

<210> SEQ ID NO 6
<211> LENGTH: 45
<212> TYPE: DNA
<213> ORGANISM: Artificial Sequence
<220> FEATURE:
<223> OTHER INFORMATION: Completely synthetic DNA Sequence

<400> SEQUENCE: 6
gaatacatgc cgatggaaag cgacggggct gaagagatgg aggtg                        45

<210> SEQ ID NO 7
<211> LENGTH: 45
<212> TYPE: DNA
<213> ORGANISM: Artificial Sequence
<220> FEATURE:
<223> OTHER INFORMATION: Completely synthetic DNA Sequence

<400> SEQUENCE: 7
cccctccatc tcttcagccc cgtcgctttc catcggcatg tattc                        45

<210> SEQ ID NO 8
<211> LENGTH: 36
<212> TYPE: DNA
<213> ORGANISM: Artificial Sequence
<220> FEATURE:
```

<223> OTHER INFORMATION: Completely synthetic DNA Sequence

<400> SEQUENCE: 8
gaattcagat ctaccatgag cgatgttacc attgtg 36

<210> SEQ ID NO 9
<211> LENGTH: 30
<212> TYPE: DNA
<213> ORGANISM: Artificial Sequence
<220> FEATURE:
<223> OTHER INFORMATION: Completely synthetic DNA Sequence

<400> SEQUENCE: 9
tctagatctt attctcgtcc acttgcagag 30

<210> SEQ ID NO 10
<211> LENGTH: 48
<212> TYPE: DNA
<213> ORGANISM: Artificial Sequence
<220> FEATURE:
<223> OTHER INFORMATION: Completely synthetic DNA Sequence

<400> SEQUENCE: 10
ggtaccatgg aatacatgcc gatggaaagc gatgttacca ttgtgaag 48

<210> SEQ ID NO 11
<211> LENGTH: 33
<212> TYPE: DNA
<213> ORGANISM: Artificial Sequence
<220> FEATURE:
<223> OTHER INFORMATION: Completely synthetic DNA Sequence

<400> SEQUENCE: 11
aagcttagat ctaccatgaa tgaggtgtct gtc 33

<210> SEQ ID NO 12
<211> LENGTH: 30
<212> TYPE: DNA
<213> ORGANISM: Artificial Sequence
<220> FEATURE:
<223> OTHER INFORMATION: Completely synthetic DNA Sequence

<400> SEQUENCE: 12
gaattcggat cctcactcgc ggatgctggc 30

<210> SEQ ID NO 13
<211> LENGTH: 49
<212> TYPE: DNA
<213> ORGANISM: Artificial Sequence
<220> FEATURE:
<223> OTHER INFORMATION: Completely synthetic DNA Sequence

<400> SEQUENCE: 13
ggtaccatgg aatacatgcc gatggaaaat gaggtgtctg tcatcaaag 49

<210> SEQ ID NO 14
<211> LENGTH: 6
<212> TYPE: PRT
<213> ORGANISM: Artificial Sequence
<220> FEATURE:
<223> OTHER INFORMATION: Completely synthetic Amino Acid Sequence

<400> SEQUENCE: 14

Glu Tyr Met Pro Met Glu
 1               5

```
<210> SEQ ID NO 15
<211> LENGTH: 13
<212> TYPE: PRT
<213> ORGANISM: Artificial Sequence
<220> FEATURE:
<223> OTHER INFORMATION: Completely synthetic Amino Acid Sequence

<400> SEQUENCE: 15 ly Gly Arg Ala Arg Thr Ser Ser Phe Ala Glu Pro Gly
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Completely synthetic Amino Acid Sequence

<400> SEQUENCE: 16

Lys Lys Gly Gly Arg Ala Arg Thr Ser Ser Phe Ala Glu Pro Gly
1               5                   10                  15
```

INHIBITORS OF AKT ACTIVITY

This application is a continuation of U.S. Ser. No. 10/473,786, filed Oct. 2, 2003 now abandoned which is a 371 of PCT/US02/10880, filed Apr. 8, 2002, which claims priority under Title 35, United States Code 119(e) from Provisional Application Ser. No. 60/282,825, filed Apr. 10, 2001.

BACKGROUND OF THE INVENTION

The present invention relates to triazolo[4,3-b]pyridazine containing compounds that are inhibitors of the activity of one or more of the isoforms of the serine/threonine kinase, Akt (also known as PKB). The present invention also relates to pharmaceutical compositions comprising such compounds and methods of using the instant compounds in the treatment of cancer.

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-$x_L$, inhibits apoptotic cell death induced by various stimuli. On the other hand, expression of pro-apoptotic genes, such as Bax or Bad, leads to programmed cell death (Aams et al. *Science*, 281:1322–1326 (1998)). The execution of programmed cell death is mediated by caspase-1 related proteinases, including caspase-3, caspase-7, caspase-8 and caspase-9 etc (Thomberry et al. *Science*, 281:1312–1316 (1998)).

The phosphatidylinositol 3'-OH kinase (PI3K)/Akt/PKB pathway appears important for regulating cell survival/cell death (Kulik et al. *Mol.Cell.Biol.* 17:1595–1606 (1997); Franke et al, *Cell*, 88:435–437 (1997); Kauffmann-Zeh et al. *Nature* 385:544–548 (1997) Hemmings *Science*, 275:628–630 (1997); Dudek et al., *Science*, 275:661–665 (1997)). Survival factors, such as platelet derived growth factor (PDGF), nerve growth factor (NGF) and insulin-like growth factor-1 (IGF-1), promote cell survival under various conditions by inducing the activity of PI3K (Kulik et al. 1997, Hemmings 1997). Activated PI3K leads to the production of phosphatidylinositol (3,4,5)-triphosphate (PtdIns (3,4,5)-P3), which in turn binds to, and promotes the activation of, the serine/threonine kinase Akt, which contains a pleckstrin homology (PH)-domain (Franke et al *Cell*, 81:727–736 (1995); Hemmings *Science*, 277:534 (1997); Downward, *Curr. Opin. Cell Biol.* 10:262–267 (1998), Alessi et al., *EMBO J.* 15: 6541–6551 (1996)). Specific inhibitors of PI3K or dominant negative Akt/PKB mutants abolish survival-promoting activities of these growth factors or cytokines. It has been previously disclosed that inhibitors of PI3K (LY294002 or wortmannin) blocked the activation of Akt/PKB by upstream kinases. In addition, introduction of constitutively active PI3K or Akt/PKB mutants promotes cell survival under conditions in which cells normally undergo apoptotic cell death (Kulik et al. 1997, Dudek et al. 1997).

Analysis of Akt levels in human tumors showed that Akt2 is overexpressed in a significant number of ovarian (J. Q. Cheung et al. *Proc. Natl. Acad. Sci. U.S.A.* 89:9267–9271 (1992)) and pancreatic cancers (J. Q. Cheung et al. *Proc. Natl. Acad. Sci. U.S.A.* 93:3636–3641 (1996)). Similarly, Akt3 was found to be overexpressed in breast and prostate cancer cell lines (Nakatani et al. *J. Biol. Chem.* 274:21528–21532 (1999)).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943–1947 (1997), Stambolic et al. *Cell* 95:29–39 (1998), Sun et al. *Proc. Natl. Acad. Sci. U.S.A.* 96:6199–6204 (1999)). Germline mutations of PTEN are responsible for human cancer syndromes such as Cowden disease (Liaw et al. *Nature Genetics* 16:64–67 (1997)). PTEN is deleted in a large percentage of human tumors and tumor cell lines without functional PTEN show elevated levels of activated Akt (Li et al. supra, Guldberg et al. *Cancer Research* 57:3660–3663 (1997), Risinger et al. *Cancer Research* 57:4736–4738 (1997)).

These observations demonstrate that the PI3K/Akt pathway plays important roles for regulating cell survival or apoptosis in tumorigenesis.

Three members of the Akt/PKB subfamily of second-messenger regulated serine/threonine protein kinases have been identified and termed Akt1/PKBα, Akt2/PKBβ, and Akt3/PKBγ respectively. The isoforms are homologous, particularly in regions encoding the catalytic domains. Akt/PKBs are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt/PKB. The current model of Akt/PKB activation proposes recruitment of the enzyme to the membrane by 3'-phosphorylated phosphoinositides, where phosphorylation of the regulatory sites of Akt/PKB by the upstream kinases occurs (B. A. Hemmings, *Science* 275: 628–630 (1997); B. A. Hemmings, *Science* 276:534 (1997); J. Downward, *Science* 279:673–674 (1998)).

Phosphorylation of Akt1/PKBI occurs on two regulatory sites, $Thr^{308}$ in the catalytic domain activation loop and on $Ser^{473}$ near the carboxy terminus (D. R. Alessi et al. *EMBO J.* 15:6541–6551 (1996) and R. Meier et al. *J. Biol. Chem.* 272:30491–30497 (1997)). Equivalent regulatory phosphorylation sites occur in Akt2/PKBβ and Akt3/PKBγ. The upstream kinase, which phosphorylates Akt/PKB at the activation loop site has been cloned and termed 3'-phosphoinositide dependent protein kinase 1 (PDK1). PDK1 phosphorylates not only Akt/PKB, but also p70 ribosomal S6 kinase, p90RSK, serum and glucocorticoid-regulated kinase (SGK), and protein kinase C. The upstream kinase phosphorylating the regulatory site of Akt/PKB near the carboxy terminus has not been identified yet, but recent reports imply a role for the integrin-linked kinase (ILK-1), a serine/threonine protein kinase, or autophosphorylation.

Inhibition of Akt activation and activity can be achieved by inhibiting PI3K with inhibitors such as LY294002 and wortmannin. However, PI3K inhibition has the potential to indiscriminately affect not just all three Akt isozymes but also other PH domain-containing signaling molecules that are dependent on PdtIns(3,4,5)-P3, such as the Tec family of tyrosine kinases. Furthermore, it has been disclosed that Akt can be activated by growth signals that are independent of PI3K.

Alternatively, Akt activity can be inhibited by blocking the activity of the upstream kinase PDK1. No specific PDK1 inhibitors have been disclosed. Again, inhibition of PDK1 would result in inhibition of multiple protein kinases whose activities depend on PDK1, such as atypical PKC isoforms, SGK, and S6 kinases (Williams et al. *Curr. Biol.* 10:439-448 (2000).

It is an object of the instant invention to provide novel compounds that are inhibitors of Akt/PKB.

It is also an object of the present invention to provide pharmaceutical compositions that comprise.

It is also an object of the present invention to provide a method for treating cancer that comprises administering such inhibitors of Akt/PKB activity.

SUMMARY OF THE INVENTION

The instant invention provides for compounds that inhibit of Akt/PKB activity. In particular, the compounds disclosed selectively inhibit one or two of the Akt/PKB isoforms. The invention also provides for compositions comprising such inhibitory compounds and methods of inhibiting Akt/PKB activity by administering the compound to a patient in need of treatment of cancer.

DETAILED DESCRIPTION OF THE INVENTION

The compounds of the instant invention are useful in the inhibition of the activity of the serine/threonine kinase Akt. In a first embodiment of this invention, the inhibitors of Akt activity are illustrated by the formula A:

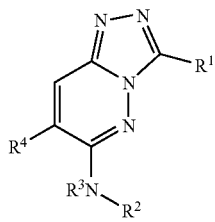

A wherein
$R^1$ represents phenyl, furyl, thienyl or pyridinyl, any of which groups may be optionally substituted with one, two or three substituents, independently selected from:
a) halogen;
b) $C_{1-4}$ alkyl;
c) $C_{1-4}$ alkoxy;
d) cyano;
e) di($C_{1-4}$ alkyl)amino;
f) hydroxy;
$R^2$ represents amino-$C_{1-6}$ alkyl, $C_{1-4}$ alkylamino-($C_{1-6}$) alkyl, di($C_{1-4}$ alkyl)amino-($C_{1-6}$)alkyl, hydroxy-($C_{1-6}$)alkyl or $C_{1-4}$ alkoxy-($C_{1-6}$)alkyl, any of which groups may be optionally substituted;
$R^3$ represents hydrogen or $C_{1-6}$ alkyl; and
$R^4$ is selected from: $C_{3-7}$ cycloalkyl and aryl, any of which groups may be optionally substituted;
or a pharmaceutically acceptable salt or stereoisomer thereof.

In another embodiment the inhibitors of the instant invention are illustrated by the formula A-I:

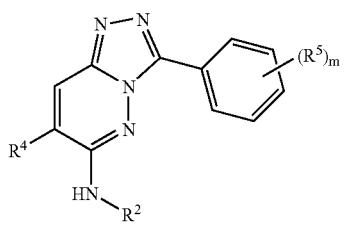

A-I wherein
$R^2$ is as defined with reference to formula I above;
$R^4$ is selected from: $C_{3-7}$ cycloalkyl and phenyl, any of which groups may be optionally substituted.
m is 0, 1, 2 or 3; and
$R^5$ independently represents halogen, $C_{1-4}$ alkyl or $C_{1-6}$ alkoxy; or a pharmaceutically acceptable salt or stereoisomer thereof.

Specific compounds of the instant invention include:
N'-(7-Cyclobutyl-3-phenyl-[1,2,4]triazolo[4,3-b]pyridazin-6-yl)-2,2,N,N-tetramethyl-propane-1,3-diamine
N'-(7-Cyclobutyl-3-(3,5-difluoro-phenyl)-[1,2,4]triazolo[4,3-b]pyridazin-6-yl)-2,2,N,N-tetramethyl-propane-1,3-diamine
N'-(7-Cyclobutyl-3-(3,4-difluoro-phenyl)-[1 2,4]triazolo[4,3-b]pyridazin-6-yl)-2,2,N,N-tetramethyl-propane-1,3-diamine
N'-(7-Cyclobutyl-3-(4-fluoro-phenyl)-[1,2,4]triazolo[4,3-b]pyridazin-6-yl)-2,2,N,N-tetramethyl-propane-1,3-diamine
N'-(7-Cyclobutyl-3-(3-fluoro-phenyl)-[1,2,4]triazolo[4,3-b]pyridazin-6-yl)-2,2,N,N-tetramethyl-propane-1,3-diamine or a pharmaceutically acceptable salt thereof.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 2,2-dimethylpropyl. Derived expressions such as "$C_{1-6}$ alkoxy" are to be construed accordingly.

As used herein, the expression "$C_{1-4}$ alkyl" includes methyl and ethyl groups, and straight-chained or branched propyl and butyl groups. Particular alkyl groups are methyl, ethyl, n-propyl, isopropyl and tert-butyl. Derived expressions such as "$C_{1-4}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

The term "halogen" as used herein includes fluorine, chlorine, bromine and iodine, especially fluorine or chlorine.

For use in medicine, the salts of the compounds of formula A will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula A above. In general, such prodrugs will be functional derivatives of the compounds of formula A that are readily convertible in vivo into the required compound of formula A. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

Examples of suitable values for the substituent $R^4$ include methyl-cyclopropyl, cyclobutyl, methyl-cyclobutyl, cyclopentyl, methyl-cyclopentyl, cyclohexyl, cyclobutenyl and phenyl.

In a particular embodiment, the substituent $R^4$ represents $C_{3-7}$ cycloalkyl or phenyl, either unsubstituted or substituted by $C_{1-6}$ alkyl or halogen, especially methyl or fluorine. Favourably, $R^4$ represents cyclobutyl or phenyl.

Examples of typical optional substituents on the group $R^1$ include methyl, fluoro and methoxy.

In a particular embodiment, $R^2$ represents amino-$C_{1-6}$ alkyl, $C_{1-4}$ alkylamino-($C_{1-6}$)alkyl or di($C_{1-4}$ alkyl)amino-($C_{1-6}$)alkyl. Representative values of $R^2$ include but are not limited to dimethylaminomethyl, aminoethyl, dimethylaminoethyl, diethylaminoethyl, 3-dimethylaminopropyl, 3-methylaminopropyl, 3-dimethylamino-2,2-dimethylpropyl and, 3-dimethylamino-2-methylpropyl.

Preferably, $R^3$ represents hydrogen or methyl.

The compounds of the instant invention are inhibitors of the activity of Akt and are thus useful in the treatment of cancer, in particular cancers associated with irregularities in the activity of Akt and/or GSK3. Such cancers include, but are not limited to ovarian, pancreatic and breast cancer.

In an embodiment of the invention, the instant compound is a selective inhibitor whose inhibitory efficacy is dependent on the PH domain. In this embodiment, the compound exhibits a decrease in in vitro inhibitory activity or no in vitro inhibitory activity against truncated Akt proteins lacking the PH domain.

In another embodiment of the invention, the instant compound is a selective inhibitor whose inhibitory efficacy is dependent on the region of the proteins between the PH domain and the kinase domain. (See Konishi et al. *Biochem. and Biophys. Res. Comm.* 216: 526–534 (1995), FIG. 2) That region will be referred to as the hinge region. In this embodiment, the compound exhibits a decrease in in vitro inhibitory activity or no in vitro inhibitory activity against truncated Akt proteins lacking the PH domain and the hinge region.

Such an inhibitor that is dependent on either the PH domain, the hinge region or both provides a particular advantage since the PH domains and hinge regions in the three Akt isoforms lack the sequence homology that is present in the rest of the protein, particularly the homology found in the kinase domains (which comprise the catalytic domains and ATP-binding consensus sequences). It is therefore observed that certain inhibitor compounds, such as those described herein, are not only selective for one or two isoforms of Akt, but also are weak inhibitors or fail to inhibit other kinases, such as PKA and PKC, whose kinase domains share some sequence homology with the kinase domains of the Akt/PKB isoforms. Both PKA and PKC lack a PH domain.

In a further embodiment, the instant compound is selected from the group of a selective inhibitor of Akt 1, a selective inhibitor of Akt 2 and a selective inhibitor of both Akt 1 and Akt 2.

In another embodiment, the instant compound is selected from the group of a selective inhibitor of Akt 1, a selective inhibitor of Akt 2, a selective inhibitor of Akt3 and a selective inhibitor of two of the three Akt isoforms.

In another embodiment, the instant compound is a selective inhibitor of all three Akt isoforms, but is not an inhibitor of one, two or all of such Akt isoforms that have been modified to delete the PH domain, the hinge region or both the PH domain and the hinge region.

The present invention is further directed to a method of inhibiting Akt activity which comprises administering to a mammal in need thereof a pharmaceutically effective amount of the instant compound.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyl-eneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution is then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

The instant compounds may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of neurofibromatosis, restinosis, polycystic kidney disease, infections of hepatitis delta and related viruses and fungal infections. The instant compositions may also be useful in combination with other inhibitors of parts of the signaling pathway that links cell surface growth factor receptors to nuclear signals initiating cellular proliferation. Thus, the instant compounds may be utilized in combination with inhibitors of prenyl-protein transferase, including protein substrate competitive inhibitors of farnesyl-protein transferase, farnesyl pyrophosphate competitive inhibitors of the activity of farnesyl-protein transferase and/or inhibitors of geranylgeranyl-protein transferase. The instant compositions may also be co-administered with compounds that are selective inhibitors of geranylgeranyl protein transferase or selective inhibitors of farnesyl-protein transferase. The instant compositions may also be administered in combination with a compound that has Raf antagonist activity.

The compounds of the instant invention may also be co-administered with other well known cancer therapeutic agents that are selected for their particular usefulness against the condition that is being treated. Included in such combinations of therapeutic agents are combinations with an antineoplastic agent. It is also understood that the instant compositions and combinations may be used in conjunction with other methods of treating cancer and/or tumors, including radiation therapy and surgery.

Examples of an antineoplastic agent include, in general, microtubule-stabilising agents (such as paclitaxel (also known as Taxol®), docetaxel (also known as Taxotere®), or their derivatives); alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Additionally, compositions of the instant invention may also be useful as radiation sensitizers. For instance, radiation therapy, including x-rays or gamma rays that are delivered from either an externally applied beam or by implantation of tiny radioactive sources, may used in combination with the instant compounds to treat cancer.

If formulated as a fixed dose, such combination products employ the combinations of this invention within the dosage range described below and the other pharmaceutically active agent(s) within its approved dosage range. The compounds of the instant invention may alternatively be used sequentially with known pharmaceutically acceptable agent(s) when a multiple combination formulation is inappropriate.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the $\alpha v\beta 3$ integrin, which selectively antagonize, inhibit or counteract binding of a physiological ligand to the $\alpha v\beta 5$ integrin, which antagonize, inhibit or counteract binding of a physiological ligand to both the $\alpha v\beta 3$ integrin and the $\alpha v\beta 5$ integrin, or which antagonize, inhibit or counteract the activity of the particular integrin(s) expressed on capillary endothelial cells. The term also refers to antagonists of the $\alpha v\beta 6$, $\alpha v\beta 8$, $\alpha 1\beta 1$, $\alpha 2\beta 1$, $\alpha 5\beta 1$, $\alpha 6\beta 1$ and $\alpha 6\beta 4$ integrins. The term also refers to antagonists of any combination of $\alpha v\beta 3$, $\alpha v\beta 5$, $\alpha v\beta 6$, $\alpha v\beta 8$, $\alpha 1\beta 1$, $\alpha 2\beta 1$, $\alpha 5\beta 1$, $\alpha 6\beta 1$ and $\alpha 6\beta 4$ integrins. The instant compounds may also be useful with other agents that inhibit angiogenisis and thereby inhibit the growth and invasiveness of tumor cells, including, but not limited to angiostatin and endostatin.

When a composition according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of the compound of the instant invention is administered to a mammal undergoing treatment for cancer. Administration occurs in an amount of inhibitor of between about 0.1 mg/kg of body weight to about 60 mg/kg of body weight per day, preferably of between 0.5 mg/kg of body weight to about 40 mg/kg of body weight per day. A particular therapeutic dosage that comprises the instant composition includes from about 0.01 mg to about 1000 mg of the instant compound. Preferably, the dosage comprises from about 1 mg to about 1000 mg of inhibitor of the instant compound.

All patents, publications and pending patent applications identified are hereby incorporated by reference.

Abbreviations used in the description of the chemistry and in the Examples that follow are:
Ac$_2$O Acetic anhydride;
Boc t-Butoxycarbonyl;
DBU 1,8-diazabicyclo[5.4.0]undec-7-ene;
TFA: trifluoroacetic acid
AA: acetic acid
Boc/BOC t-Butoxycarbonyl;
diH$_2$0 deionized water
DMA dimethylacetamide
DMF Dimethylformamide;
DMSO dimethyl sulfoxide;
EDC   1-(3-dimethylaminopropyl)-3-ethyl-carbodiimide hydrochloride;
EtOAc Ethyl acetate;
EtOH Ethanol;
FAB Fast atom bombardment;
HOAt 1-Hydroxy-7-azabenzotriazole
HOBt 1-Hydroxybenzotriazole hydrate;
HOPO 2-hydroxypyridine-N-oxide
HPLC High-performance liquid chromatography;
IPAc isopropylacetate
MeOH methanol
RPLC Reverse Phase Liquid Chromatography
THF Tetrahydrofuran.

Reactions used to generate the compounds of this invention are prepared by employing reactions as shown in the Schemes 1–3, in addition to other standard manipulations such as ester hydrolysis, cleavage of protecting groups, etc., as may be known in the literature or exemplified in the experimental procedures. Substituents R and R$^a$, as shown in the Schemes, represent the substituents $R^1$ and $R^2$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Schemes.

Synopsis of Schemes 1–3:

The requisite intermediates are in some cases commercially available, or can be prepared according to literature procedures. As illustrated in Reaction Scheme-1, a suitably substituted phenylmaleic anyhydride I is treated with hydrazine to form the dihydropyridazone dione II. Subsequent oxidative chlorination and reaction with a suitably substituted benzoic hydrazide provide the 6-chloro triazolo [4,3-b]pyridazine III. This intermediate can then be treated with a variety of amines to provide the instant compound IV.

Reaction Scheme 2 illustrates preparation of compounds of the instant invention having a cycloalkyl substituent at the 7-position. While a cyclobutyl group is illustrated, the sequence of reactions is generally applicable to incorporation of a variety of unsubstituted or substituted cycloalkyl moieties. Thus, 3,6-dichloro-pyridazine is alkylated via silver catalyzed oxidative decarboxylation with cyclobutyl carboxylic acid to provide the cyclobutyl dicloropyridazine V, which then undergoes the reactions described above to provide the instant compound VI.

Reaction Scheme 3 illustrates an alternative preparation of the instant compounds (*Tetrahedron Letters* 41:781–784 (2000)).

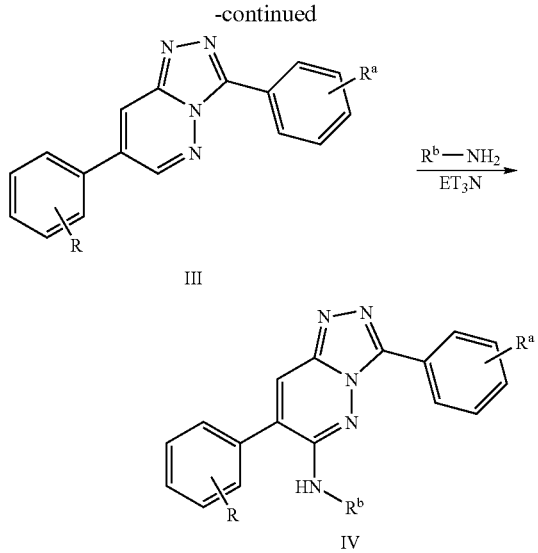

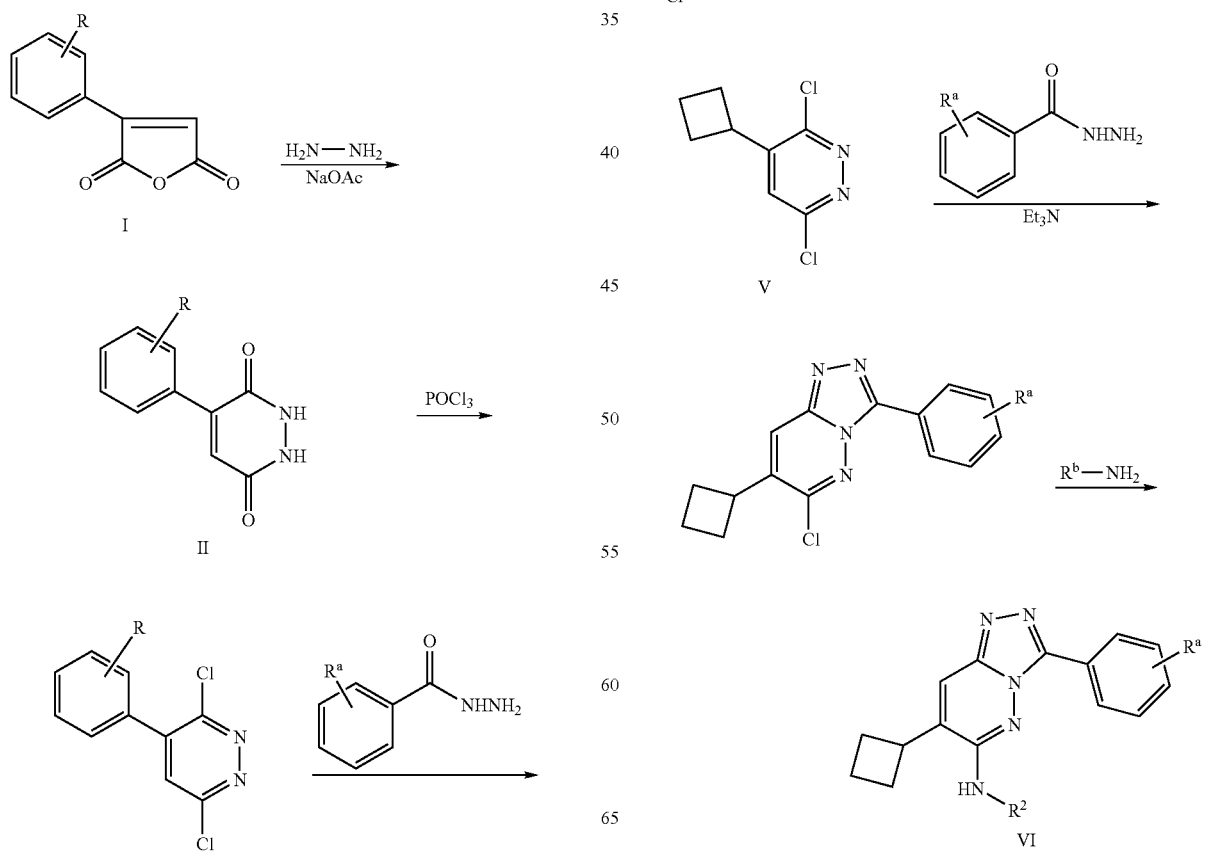

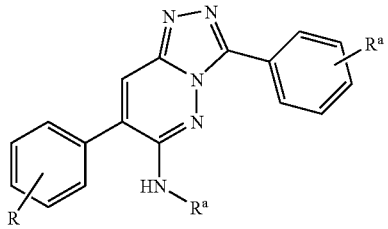

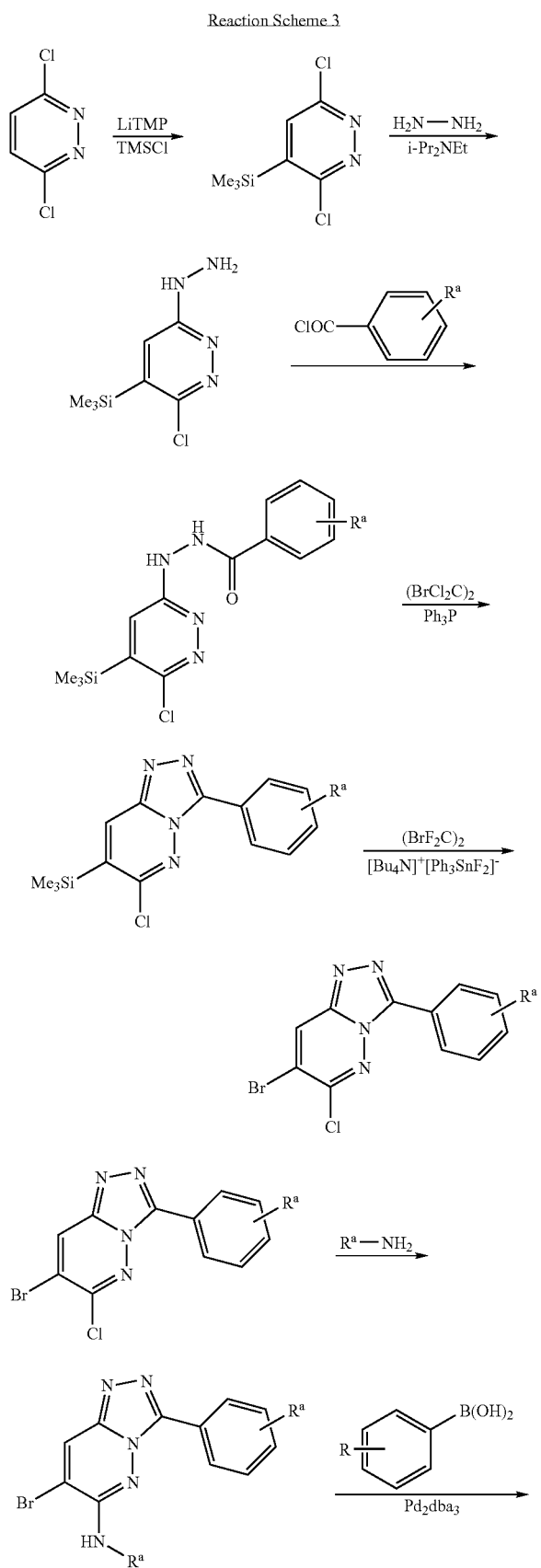

EXAMPLES

Examples provided are intended to assist in a further understanding of the invention. Particular materials employed, species and conditions are intended to be further illustrative of the invention and not limitative of the reasonable scope thereof.

Examples 1

N'-(7-Cyclobutyl-3-phenyl-[1,2,4]triazolo[4,3-b]pyridazin-6-yl)-2,2,N,N-tetramethyl-propane-1,3-diamine (Compound 1)

Step 1: 3,6-Dichloro-4-cyclobutylpyridazine

Concentrated sulphuric acid (53.6 ml, 1.0 mol) was added carefully to a stirred suspension of 3,6-dichloropyridazine (50.0 g, 0.34 mol) in water (1.25 l). This mixture was then heated to 70° C. (internal temperature) before the addition of cyclobutane carboxylic acid (35.3 ml, 0.37 mol). A solution of silver nitrate (11.4 g, 0.07 mol) in water (20 ml) was then added over approximately one minute. This caused the reaction mixture to become milky in appearance. A solution of ammonium persulphate (230 g, 1.0 mol) in water (0.63 l) was then added over 20–30 minutes. The internal temperature rose to approximately 85° C. During the addition the product formed as a sticky precipitate. Upon complete addition the reaction was stirred for an additional 5 minutes, then allowed to cool to room temperature. The mixture was then poured onto ice and basified with concentrated aqueous ammonia, with the addition of more ice as required to keep the temperature below 10° C. The aqueous phase was extracted with dichloromethane (×3). The combined extracts were dried (MgSO$_4$), filtered and evaporated to give the title compound (55.7 g, 82%) as an oil. $^1$H nmr (CDCl$_3$) indicated contamination with approximately 5% of the 4,5-dicyclobutyl compound. However, this material was used without further purification. Data for the title compound: $^1$H NMR (360 MHz, d$_6$-DMSO) δ1.79–1.90 (1H, m), 2.00–2.09 (1H, m), 2.18–2.30 (2H, m), 2.33–2.40 (2H, m), 3.63–3.72 (1H, m), 7.95 (1H, s); MS (ES$^+$) m/e 203 [MH]$^+$, 205 [MH]$^+$, 207 [MH]$^+$.

Step 2: 6-Chloro-7-cyclobutyl-3-phenyl-1,2,4-triazolo[4,3-b]pyridazine

A mixture of 3,6-dichloro-4-cyclobutylpyridazine from above (55.7 g, 0.27 mol), benzoic hydrazide (41.1 g, 0.30 mol) and triethylamine hydrochloride (41.5 g, 0.30 mol) in p-xylene (0.4 l) was stirred and heated at reflux under a stream of nitrogen for 24 hours. Upon cooling the volatiles were removed in vacuo. The residue was partitioned between dichloromethane and water. The aqueous was basified by the addition of solid potassium carbonate. Some dark insoluble material was removed by filtration at this stage. The aqueous phase was further extracted with dichloromethane (×2). The combined extracts were dried (MgSO$_4$), filtered and evaporated. The residue was purified by chromatography on silica gel eluting with 5%→10%→25% ethyl acetate/dichloromethane to give the title compound, (26.4 g, 34%) as an off-white solid. Data for the title compound: $^1$H NMR (360 MHz, CDCl$_3$) δ 1.90–2.00 (1H, m), 2.12–2.28 (3H, m), 2.48–2.57 (2H, m), 3.69–3.78 (1H, m), 7.49–7.59 (3H, m), 7.97 (1H, s), 8.45–8.48 (2H, m); MS (ES$^+$) m/e 285 [MH]$^+$, 287 [MH]$^+$.

Step 3: N'-(7-Cyclobutyl-3-phenyl-[1,2,4]triazolo[4,3-b]pyridazin-6-yl)-2,2,N,N-tetramethyl-propane-1,3-diamine 6-Chloro-7-cyclobutyl-3-phenyl-[1,2,4]triazolo[4,3-b]pyridazine (100 mg) and N,N,2,2-tetramethyl-1,3-propanediamine (2 ml) were heated together in a sealed tube at 70° C. for 16 hours. Cooled and water (5 ml) added. Precipitate filtered, washed (water, ether) and dried. $^1$H NMR (250 MHz, DMSO) δ 1.20 (6H, s), 2.10 (1H, m), 2.24–2.65 (14H, m), 3.53–3.70 (2H, m), 7.69–7.82 (4H, m), 8.03 (1H,s), 8.70 (2H, m). MS (ES+) MH$^+$=379

Example 2

N'-(7-Cyclobutyl-3-(3,5-difluoro-phenyl)-[1,2,4]triazolo[4,3-b]pyridazin-6-yl)-2,2,N,N-tetramethyl-propane-1,3-diamine (Compound 2)

The title compound was prepared in an analogous fashion to Example 1, except substituting 3,5-difluorobenzoic hydrazine for the benzoic hydrazine in Step 2. $^1$H NMR (360 MHz, CDCl$_3$) δ 1.07 (6H, s), 1.99 (1H, m), 2.10–2.50 (13H, m), 3.31–3.35 (3H, m), 6.84–6.89 (1H, m), 7.63 (1H, s), 7.90 (1H, vbs), 8.20–8.23 (2H,m). MS (ES+) MH$^+$=415

Example 3

N'-(7-Cyclobutyl-3-(3,4-difluoro-phenyl)-[1,2,4]triazolo[4,3-b]pyridazin-6-yl)-2,2,N,N-tetramethyl-propane-1,3-diamine (Compound 3)

The title compound was prepared in an analogous fashion to Example 1, except substituting 3,4-difluorobenzoic hydrazine for the benzoic hydrazine in Step 2. $^1$H NMR (360 MHz, CDCl$_3$) δ 1.07 (6H, s), 1.99–2.49 (14H, m), 3.30–3.33 (3H, m), 7.25–7.30 (1H, m), 7.62 (1H, s), 7.87 (1H, vbs), 8.32–8.34 (1H, m), 8.51–8.57 (1H,m). MS (ES+) MH$^+$=415

Example 4

N'-(7-Cyclobutyl-3-(4-fluoro-phenyl)-[1,2,4]triazolo[4,3-b]pyridazin-6-yl)-2,2,N,N-tetramethyl-propane-1,3-diamine (Compound 4)

The title compound was prepared in an analogous fashion to Example 1, except substituting 4-fluorobenzoic hydrazine for the benzoic hydrazine in Step 2.

$^1$H NMR (360 MHz, CDCl$_3$) δ 1.06 (6H, s), 1.98–2.49 (14H, m), 3.31–3.32 (3H, m), 7.18–7.26 (2H, m), 7.61 (1H, s), 7.80 (1H, vbs), 8.55–8.59 (2H, m). MS (ES+) MH$^+$=397

Example 5

N'-(7-Cyclobutyl-3-(3-fluoro-phenyl)-[1,2,4]triazolo[4,3-b]pyridazin-6-yl)-2,2,N,N-tetramethyl-propane-1,3-diamine (Compound 5)

The title compound was prepared in an analogous fashion to Example 1, except substituting 3-fluorobenzoic hydrazine for the benzoic hydrazine in Step 2.

$^1$H NMR (360 MHz, CDCl$_3$) δ 1.07 (6H, s), 1.96–2.50 (14H, m), 3.31–3.35 (3H, m), 7.10–7.15 (1H, m), 7.44–7.50 (1H, m), 7.63 (1H, m) 7.81 (1H, vbs), 8.35–8.42 (2H, m). MS (ES+) MH$^+$=397

Example 6

Cloning of the human Akt isoforms and ΔPH-Akt1

The pS2neo vector (deposited in the ATCC on Apr. 3, 2001 as ATCC) was prepared as follows: The pRmHA3 vector (prepared as described in *Nucl. Acid Res.* 16:1043–1061 (1988)) was cut with BglII and a 2734 bp fragment was isolated. The pUChsneo vector (prepared as described in *EMBO J.* 4:167–171 (1985)) was also cut with BglII and a 4029 bp band was isolated. These two isolated fragments were ligated together to generate a vector termed pS2neo-1. This plasmid contains a poly-linker between a metallothionine promoter and an alcohol dehydrogenase poly A addition site. It also has a neo resistance gene driven by a heat shock promoter. The pS2neo-1 vector was cut with Psp5II and BsiWI. Two complementary oligonucleotides were synthesized and then annealed (CTGCGGCCGC (SEQ.ID.NO.: 1) and GTACGCGGCCGCAG (SEQ.ID.NO.: 2)). The cut pS2neo-1 and the annealed oligonucleotides were ligated together to generate a second vector, pS2neo. Added in this conversion was a NotI site to aid in the linearization prior to transfection into S2 cells.

Human Akt1 gene was amplified by PCR (Clontech) out of a human spleen cDNA (Clontech) using the 5' primer: 5'CGCGAATTCAGATCTACCASTEAGCGACGTGGCT ATTGTG 3' (SEQ.ID.NO.: 3), and the 3' primer: 5'CGCTCT AGAGGATCCTCAGGCCGTGCTGCTGGC3' (SEQ.ID.NO.: 4). The 5' primer included an EcoRI and BglII site. The 3' primer included an XbaI and BamHI site for cloning purposes. The resultant PCR product was subcloned into pGEM3Z (Promega) as an EcoRI/Xba I fragment. For expression/purification purposes, a middle T tag was added to the 5' end of the full length Akt1 gene using the PCR primer: 5'GTACGATGCTGAACGATATCTTCG 3' (SEQ.ID.NO.: 5). The resulting PCR product encompassed a 5' KpnI site and a 3' BamHI site which were used to subclone the fragment in frame with a biotin tag containing insect cell expression vector, pS2neo.

For the expression of a pleckstrin homology domain (PH) deleted (Δ aa 4–129, which includes deletion of a portion of the Akt1 hinge region) version of Akt1, PCR deletion mutagenesis was done using the full length Akt1 gene in the pS2neo vector as template. The PCR was carried out in 2 steps using overlapping internal primers (5' GAATACATGC CGATGGAAAGCGACΔGGGGCTGAAGAGATGGAGG TG 3' (SEQ.ID.NO.:6), and 5' CCCCTCCATCTCTTCAGC CCCΔGTCGCTTTCCATCGGCATGTATTC 3' (SEQ.ID.NO.: 7)) which encompassed the deletion and 5' and 3' flanking primers which encompassed the KpnI site and middle T tag on the 5' end. The final PCR product was digested with KpnI and SmaI and ligated into the pS2neo full length Akt1 KpnI/Sma I cut vector, effectively replacing the 5' end of the clone with the deleted version.

Human Akt3 gene was amplified by PCR of adult brain cDNA (Clontech) using the amino terminal oligo primer:

```
                                    (SEQ.ID.NO.: 8)
  5' GAATTCAGATCTACCATGAGCGATGTTACCATTGTG 3';
  and
```

```
                                    (SEQ.ID.NO.: 9)
  the carboxy terminal oligo primer:
  5' TCTAGATCTTATTCTCGTCCACTTGCAGAG 3'.
```

These primers included a 5' EcoRI/BglII site and a 3' XbaI/BglII site for cloning purposes. The resultant PCR product was cloned into the EcoRI and XbaI sites of pGEM4Z (Promega). For expression/purification purposes, a middle T tag was added to the 5' end of the full length Akt3 clone using the PCR primer: 5' GGTACCATGGAATA-CATGCCGATGGAAAGCGATGTTACCATTGTGAAG 3' (SEQ.ID.NO.: 10). The resultant PCR product encompassed a 5' KpnI site which allowed in frame cloning with the biotin tag containing insect cell expression vector, pS2neo.

Human Akt2 gene was amplified by PCR from human thymus cDNA (Clontech) using the amino terminal oligo primer: 5' AAGCTTAGATCTACCATGAATGAGGT-GTCTGTC 3' (SEQ.ID.NO.: 11); and the carboxy terminal oligo primer: 5' GAATTCGGATCCTCACTCGCGGAT-GCTGGC 3' (SEQ.ID.NO.: 12). These primers included a 5' HindIII/BglII site and a 3' EcoRI/BamHI site for cloning purposes. The resultant PCR product was subcloned into the HindIII/EcoRI sites of pGem3Z (Promega). For expression/purification purposes, a middle T tag was added to the 5' end of the full length Akt2 using the PCR primer: 5' GGTAC-CATGGAATACATGCCGATGGAAAATGAG-GTGTCTGTCATCAAAG 3' (SEQ.ID.NO.: 13). The resultant PCR product was subcloned into the pS2neo vector as described above.

Example 7

Expression of human Akt isoforms and ΔPH-Akt1

The DNA containing the cloned Akt1, Akt2, Akt3 and ΔPH-Akt1 genes in the pS2neo expression vector was purified and used to transfect *Drosophila* S2 cells (ATCC) by the calcium phosphate method. Pools of antibiotic (G418, 500 μg/ml) resistant cells were selected. Cell were expanded to a 1.0 L volume (~7.0×10$^6$/ml), biotin and CuSO$_4$ were added to a final concentration of 50 μM and 50 mM respectively. Cells were grown for 72 h at 27° C. and harvested by centrifugation. The cell paste was frozen at −70 C until needed.

Example 8

Purification of human Akt isoforms and ΔPH-Akt1

Cell paste from one liter of S2 cells, described in Example 13, was lysed by sonication with 50 mls 1% CHAPS in buffer A: (50 mM Tris pH 7.4, 1 mM EDTA, 1 mM EGTA, 0.2 mM AEBSF, 10 μg/ml benzamidine, 5 μg/ml of leupeptin, aprotinin and pepstatin each, 10% glycerol and 1 mM DTT). The soluble fraction was purified on a Protein G Sepharose fast flow (Pharmacia) column loaded with 9 mg/ml anti-middle T monoclonal antibody and eluted with 75 μM EYMPME (SEQ.ID.NO.: 14) peptide in buffer A containing 25% glycerol. Akt/PKB containing fractions were pooled and the protein purity evaluated by SDS-PAGE. The purified protein was quantitated using a standard Bradford protocol. Purified protein was flash frozen on liquid nitrogen and stored at −70° C.

Example 9

Kinase Assays

This procedure describes a kinase assay which measures phosphorylation of a biotinylated GSK3-derived peptide by human recombinant active Akt/PBK isoforms or Akt/PBK mutants. The $^{33}$P-labeled biotinylated product can be captured and detected using Streptavidin coated Flashplates (NEN LifeSciences) or Streptavidin Membrane Filter Plates (Promega). Alternatively, a GSK3-derived peptide with 2 added lysine residues was used as the substrate and subsequently captured using Phosphocellulose Membrane Filter Plates (Polyfiltronics).

Materials:

Active human Akt: The following active human Akt isoforms were utilized in the in vitro assays: active human Akt1 (obtained from Upstate Biotechnology, catalog no. 14-276, 15 μg/37 μl (6.76 μM)) or recombinant lipid activated Akt1 (prepared as described in Example 8); Akt2 (prepared as described in Example 8); Akt3 (prepared as described in Example 8); and delta PH-Akt1 (prepared as described in Example 8).

Akt specific peptide substrate: GSK3α (S21) Peptide #3928, biotin-GGRARTSSFAEPG (SEQ.ID.NO.: 15), FW=1517.8 (obtained from Macromolecular Resources) for Streptavidin Flashplate or Streptavidin Filter Plate detection.

GSK3α (S21) Peptide #G80613, KKGGRARTSSFAEPG (SEQ.ID.NO.: 14), FW=1547.8 (obtained from Research Genetics) for Phosphocellulose filter plate detection.

Standard Assay Solutions:
A. 10× Assay Buffer: 500 mM HEPES, pH 7.5
  1% PEG
  1 mM EDTA
  1 mM EGTA
  20 mM β-Glycerol phosphate
B. Active Akt (500 nM): Diluent (1× Assay buffer, 10% glycerol, 0.1% β-mercaptoethanol, 1.0 μM microcystin LR and 1.0 mM EDTA) was added to a vial containing 37 μl of active Akt isoform (6.76 μM). Aliquots were flash frozen in liquid N$_2$ and stored at −70° C.
C. 1 mM Akt specific peptide substrate in 50 mM Tris pH 7.5, 1 mM DTT.
D. 100 mM DTT in di H$_2$O.
E. 100× Protease Inhibitor Cocktail (PIC): 1 mg/ml benzamidine, 0.5 mg/ml pepstatin, 0.5 mg/ml leupeptin, 0.5 mg/ml aprotinin.
F. 3 mM ATP, 200 mM MgCl$_2$ in H$_2$O, pH 7.9.
G. 50% (v/v) Glycerol.
H. 1% (wt/v) BSA (10 mg/ml) in diH20, 0.02% (w/v) NaN$_3$.
I. 125 mM EDTA.
J. 0.75% (wt/v) Phosphoric Acid.
K. 2.5 M Potassium Chloride.
L. Tris Buffered Saline (TBS), 25 mM Tris, 0.15 M Sodium Chloride, pH 7.2 (BupH Tris Buffered Saline Pack, Pierce catalog no. 28376).

Procedure for Streptavidin Flash Plate Assay:

Step 1:
A 1 μl solution of the test compound in 100% DMSO was added to 20 μl of 2× substrate solution (20 uM GSK3 Peptide, 300 μM ATP, 20 mM MgCl$_2$, 20 μCi/ml [γ$^{33}$P] ATP, 1× Assay Buffer, 5% glycerol, 1 mM DTT, 1× PIC, 0.1% BSA and 100 mM KCl). Phosphorylation reactions were initiated by adding 19 μl of 2× Enzyme solution (6.4 nM active Akt/PKB, 1× Assay Buffer, 5% glycerol, 1 mM DTT, 1× PIC and 0.1% BSA). The reactions were then incubated at room temperature for 45 minutes.

Step 2:
The reaction was stopped by adding 170 μl of 125 mM EDTA. 200 μl of stopped reaction was transferred to a Streptavidin Flashplate® PLUS (NEN Life Sciences, catalog no. SMP103). The plate was incubated for ≧10 minutes at room temperature on a plate shaker. The contents of each well was aspirated, and the wells rinsed 2 times with 200 μl TBS per well. The wells were then washed 3 times for 5 minutes with 200 μl TBS per well with the plates incubated at room temperature on a platform shaker during wash steps.

The plates were covered with sealing tape and counted using the Packard TopCount with the appropriate settings for counting [$^{33}$P] in Flashplates.

Procedure for Streptavidin Filter Plate Assay:

Step 1:
The enzymatic reactions as described in Step 1 of the Streptavidin Flash Plate Assay above were performed.

Step 2:
The reaction was stopped by adding 20 μl of 7.5M Guanidine Hydrochloride. 50 μl of the stopped reaction was transferred to the Streptavidin filter plate (SAM$^2$™ Biotin Capture Plate, Promega, catalog no. V7542) and the reaction was incubated on the filter for 1–2 minutes before applying vacuum.

The plate was then washed using a vacuum manifold as follows: 1) 4×200 μl/well of 2M NaCl; 2) 6×200 μl/well of 2M NaCl with 1% $H_3PO_{4b1;3}$) 2×200 μl/well of di$H_2O$; and 4) 2×100 μl/well of 95% Ethanol. The membranes were then allowed to air dry completely before adding scintillant.

The bottom of the plate was sealed with white backing tape, 30 μl/well of Microscint 20 (Packard Instruments, catalog no. 6013621) was added. The top of the plate was sealed with clear sealing tape, and the plate then counted using the Packard TopCount with the appropriate settings for [$^{33}$P] with liquid scintillant.

Procedure for Phosphocellulose Filter Plate Assay:

Step 1:
The enzymatic reactions were performed as described in Step 1 of the Streptavidin Flash Plate Assay (above) utilizing KKGGRARTSSFAEPG (SEQ.ID.NO.: 16) as the substrate in place of biotin-GGRARTSSFAEPG.

Step 2:
The reaction was stopped by adding 20 μl of 0.75% $H_3PO_4$. 50 μl of stopped reaction was transferred to the filter plate (UNIFILTER™, Whatman P81 Strong Cation Exchanger, White Polystyrene 96 Well Plates, Polyfiltronics, catalog no. 7700-3312) and the reaction incubated on the filter for 1–2 minutes before applying vacuum.

The plate was then washed using a vacuum manifold as follows: 1) 9×200 μl/well of 0.75% $H_3PO_4$; and 2) 2×200 μl/well of di$H_2O$. The bottom of the plate was sealed with white backing tape, then 30 μl/well of Microscint 20 was added. The top of the plate was sealed with clear sealing tape, and the plate counted using the Packard TopCount with the appropriate settings for [$^{33}$P] and liquid scintillant.

PKA Assay

Each individual PKA assay consists of the following components:
1) 10 μl 5× PKA assay buffer (200 mM Tris pH7.5, 100 mM $MgCl_2$, 5mM 2-mercaptoethanol, 0.5 mM EDTA)
2) 10 Tl of a 50 μM stock of Kemptide (Sigma) diluted into water
3) 10 μl $^{33}$P-ATP (prepared by diluting 1.0 μl $^{33}$P-ATP [10 mCi/ml] into 200 Tl of a 50 μM stock of unlabeled ATP)
4) 10 μl appropriate solvent control dilution or inhibitor dilution
5) 10 μl of a 70 nM stock of PKA catalytic subunit (UBI catalog # 14-114) diluted in 0.5 mg/ml BSA The final assay concentrations were 40 mM Tris pH 7.5, 20 mM $MgCl_2$, 1 mM 2-mercaptoethanol, 0.1 mM EDTA, 10 μM Kemptide, 10 μM $^{33}$P-ATP, 14 nM PKA and 0.1 mg/ml BSA.

Assays were assembled in 96 deep-well assay plates. Components #3 and #4 were premixed and in a separate tube, a mixture containing equal volumes of components #1, #2, and #5 was prepared. The assay reaction was initiated by adding 30 μl of the components #1, #2, and #5 mixture to wells containing $^{33}$P-ATP and inhibitor. The liquid in the assay wells was mixed and the assay reactions incubated for 20 minutes at room temperature. The reactions were stopped by adding 50 μl 100 mM EDTA and 100 mM sodium pyrophosphate and mixing.

The enzyme reaction product (phosphorylated Kemptide) was quantitated using p81 phosphocellulose 96 well filter plates (Millipore). Each well of a p81 filter plate was filled with 75 mM phosphoric acid. The wells were aspirated and 170 μl of 75 mM phosphoric acid was added to each well. A 30–40 μl aliquot from each stopped PKA reaction was added to corresponding wells on the filter plate containing the phosphoric acid. The peptide was trapped on the filter following the application of a vacuum. The filters were washed 5× by filling wells with 75 mM phosphoric acid followed by aspiration. After the final wash, the filters were allowed to air dry. 30 μl scintillation fluid was added to each well and the filters counted on a TopCount (Packard).

PKC Assay

Each PKC assay consists of the following components:
1) 5 μl 10× PKC co-activation buffer (2.5 mM EGTA, 4 mM $CaCl_2$)
2) 10 μl 5× PKC activation buffer (1.6 mg/ml phosphatidylserine, 0.16 mg/ml diacylglycerol, 100 mM Tris pH 7.5, 50 mM MgCl, 5 mM 2-mercaptoethanol)
3) 5 μl $^{33}$P-ATP (prepared by diluting 1.0 μl $^{33}$P-ATP [10 mCi/ml] into 100 μl of a 100 TM stock of unlabeled ATP)
4) 10 μl of a 350 μg/ml stock of myelin basic protein (MBP, UBI) diluted in water
5) 10 μl appropriate solvent control or inhibitor dilution
6) 10 μl of a 50 ng/ml stock of PKC (mix of isoforms from UBI catalog #14-115) diluted into 0.5 mg/ml BSA Final assay concentrations were as follows: 0.25 mM EGTA, 0.4 mM CaCl, 20 mM Tris pH 7.5, 10 mM MgCl, 1 mM 2-mercaptoethanol, 0.32 mg/ml phosphatidylserine, 0.032 mg/ml diacylglycerol, 10 μM $^{33}$P-ATP, 70 μg/ml MBP, 10 ng/ml PKC, 0.1 mg/ml BSA.

Assays are performed using 96 deep well assay plates. In each assay well 10 μl of solvent control or appropriate inhibitor dilution with 5 μl $^{33}$P-ATP (components #5 and #3) were premixed. In a separate tube, a mixture containing equal volumes of components #1, #2, #4, and #6 was prepared. The assay reaction was initiated by adding 35 μL of the components #1, #2, #4, and #6 mixture to wells containing $^{33}$P-ATP and inhibitor. The liquid in the assay wells was thoroughly mixed and the assay reactions incubated for 20 minutes at room temperature. The reactions were stopped by adding 100 mM EDTA (50 μl) and 100 mM sodium pyrophosphate (50 μl) and mixing. Phosphorylated MBP was collected on PVDF membranes in 96 well filter plates and quantitated by scintillation counting.

The results from testing the compounds described in Examples 1–5 in the assays described above are shown in Table 1:

TABLE 1

| | GSK3 Peptide Substrate IC$_{50}$ (μM) | | | | Counter screens IC$_{50}$ (μM) | |
|---|---|---|---|---|---|---|
| | Akt-1 delta | | | | | |
| | Akt-1 | PH | Akt2 | Akt3 | PKA | PKC |
| Compound 1 | 1.4 | >50 | >50 | >50 | >40 | >40 |
| Compound 2 | 0.42 | >50 | >50 | >50 | >40 | >40 |
| Compound 3 | 0.91 | >50 | >50 | >50 | >40 | >40 |
| Compound 4 | 2.03 | >50 | >50 | >50 | >40 | >40 |
| Compound 5 | 0.4 | >50 | >50 | >50 | >40 | >40 |

Example 10

Cell based Assays to Determine Inhibition of Akt/PKB

Cells (for example LnCaP or a PTEN$^{(-/-)}$tumor cell line with activated Akt/PKB) were plated in 100 mM dishes. When the cells were approximately 70 to 80% confluent, the cells were refed with 5mls of fresh media and the test compound added in solution. Controls included untreated cells, vehicle treated cells and cells treated with either LY294002(Sigma) or wortmanin (Sigma) at 20 μM or 200 nM, respectively. The cells were incubated for 2 hrs, and the media removed, The cells were washed with PBS, scraped and transferred to a centrifuge tube. They were pelleted and washed again with PBS. Finally, the cell pellet was resuspended in lysis buffer (20 mM Tris pH8, 140 mM NaCl, 2 mM EDTA, 1% Triton, 1 mM Na Pyrophosphate, 10 mM β-Glycerol Phosphate, 10 mM NaF, 0.5 mm NaVO$_4$, 1 μM Microsystine, and 1× Protease Inhibitor Cocktail), placed on ice for 15 minutes and gently vortexed to lyse the cells. The lysate was spun in a Beckman tabletop ultra centrifuge at 100,000×g at 4° C. for 20 min. The supernatant protein was quantitated by a standard Bradford protocol (BioRad) and stored at −70° C. until needed.

Proteins were immunoprecipitated (IP) from cleared lysates as follows: For Akt1/PKBI, lysates are mixed with Santa Cruz sc-7126 (D-17) in NETN (100 mM NaCl, 20 mM Tris pH 8.0, 1 mM EDTA, 0.5% NP-40) and Protein A/G Agarose (Santa Cruz sc-2003) was added. For Akt2/PKBβ, lysates were mixed in NETN with anti-Akt-2 agarose (Upstate Biotechnology #16-174) and for Akt3/PKBγ, lysates were mixed in NETN with anti-Akt-3 agarose (Upstate Biotechnology #16-175). The IPs were incubated overnight at 4° C., washed and seperated by SDS-PAGE.

Western blots were used to analyze total Akt, pThr308 Akt, pSer473 Akt, and downstream targets of Akt using specific antibodies (Cell Signaling Technology): Anti-Total Akt (cat. no. 9272), Anti-Phopho Akt Serine 473 (cat. no. 9271), and Anti-Phospho Akt Threonine 308 (cat. no. 9275). After incubating with the appropriate primary antibody diluted in PBS+0.5% non-fat dry milk (NFDM) at 4° C. overnight, blots were washed, incubated with Horseradish peroxidase (HRP)-tagged secondary antibody in PBS+0.5% NFDM for 1 hour at room temperature. Proteins were detected with ECL Reagents (Amersham/Pharmacia Biotech RPN2134).

Example 11

Heregulin Stimulated Akt Activation

MCF7 cells (a human breast cancer line that is PTEN$^{+/+}$) were plated at 1×10$^6$ cells per 100 mM plate. When the cells were 70–80% confluent, they were refed with 5 ml of serum free media and incubated overnight. The following morning, compound was added and the cells were incubated for 1–2 hrs, heregulin was added (to induce the activation of Akt) for 30 minutes and the cells were analyzed as described above.

Example 12

Inhibition Of Tumor Growth

In vivo efficacy of an inhibitor of the growth of cancer cells may be confirmed by several protocols well known in the art.

Human tumor cell lines which exhibit a deregulation of the PI3K pathway (such as LnCaP, PC3, C33a, OVCAR-3, MDA-MB-468 or the like) are injected subcutaneously into the left flank of 8–12 week old female nude mice (Harlan) on day 0. The mice are randomly assigned to a vehicle, compound or combination treatment group. Daily subcutaneous administration begins on day 1 and continues for the duration of the experiment. Alternatively, the inhibitor test compound may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 4 to 5.5 weeks after the cells were injected. The average weight of the tumors in each treatment group for each cell line is calculated.

What is claimed is:

1. A method of treating cancer selected from the groups consisting of ovarian, pancreatic and breast cancer which comprises administering to a mammal a therapeutically effective amount of a compound which is selected from:
   N'-(7-Cyclobutyl-3-phenyl-[1,2,4]triazolo[4,3-b]pyridazin-6-yl)-2,2,N,N-tetramethyl-propane-1,3-diamine;
   N'-(7-Cyclobutyl-3-(3,5-difluoro-phenyl)-[1,2,4]triazolo[4,3-b]pyridazin-6-yl)-2,2,N,N-tetramethyl-propane-1,3-diamine;
   N'-(7-Cyclobutyl-3-(3,4-difluoro-phenyl)-[1,2,4]triazolo[4,3-b]pyridazin-6-yl)-2,2,N,N-tetramethyl-propane-1,3-diamine;
   N'-(7-Cyclobutyl-3-(4-fluoro-phenyl)-[1,2,4]triazolo[4,3-b]pyridazin-6-yl)-2,2,N,N-tetramethyl-propane-1,3-diamine; and
   N'-(7-Cyclobutyl-3-(3-fluoro-phenyl)-[1,2,4]triazolo[4,3-b]pyridazin-6-yl)-2,2,N,N-tetramethyl-propane-1,3-diamine;
or a pharmaceutically acceptable salt thereof.

2. A method of treating cancer selected from the groups consisting of varian, pancreatic and breast cancer which comprises administering to a mammal a therapeutically effective amount of a pharmaceutical composition comprising a pharmaceutical carrier, and dispered therein, a compound which is selected from:
   N'-(7-Cyclobutyl-3-phenyl-1,2,4triazolo[4,3-b]pyridazin-6-yl)-2,2,N,N-tetramethyl-propane-1,3-diamine;
   N'-(7-Cyclobutyl-3-(3,5-difluoro-phenyl)-[1,2,4]triazolo[4,3-b]pyridazin-6-yl)-2,2,N,N-tetramethy-propane-1,3-diamine;
   N'-(7-Cyclobutyl-3-(3,4-difluoro-phenyl)-[1,2,4]triazolo[4,3-b]pyridazin-6-yl)-2,2,N,N-tetramethyl-propane-1,3-diamine;
   N'-(7-Cyclobutyl-3-(4-fluoro-phenyl)-[1,2,4]triazolo[4,3-b]pyridazin-6-yl)-2,2,N,N-tetramethyl-propane-1,3-diamine; and
   N'-(7-Cyclobutyl-3-(3-fluoro-phenyl)-[1,2,4]triazolo[4,3-b]pyridazin-6-yl)-2,2,N,N-tetramethyl-propane-1,3-diamine;
or a pharmaceutically acceptable salt thereof.

* * * * *

UNITED STATES PATENT AND TRADEMARK OFFICE
CERTIFICATE OF CORRECTION

PATENT NO. : 7,098,208 B2
APPLICATION NO. : 11/234784
DATED : August 29, 2006
INVENTOR(S) : Andrew Pate Owens and Stanley F. Barnett It is certified that error appears in the above-identified patent and that said Letters Patent is hereby corrected as shown below:

(1) On the Title page, item (73) Assignee should read:
Item
--(73)  Merck & Co., Inc. Rahway, NJ (US) and Merck Sharpe & Dohme Ltd. Hertfordshire (UK)--

Signed and Sealed this

Nineteenth Day of February, 2008

JON W. DUDAS
*Director of the United States Patent and Trademark Office*